(12) United States Patent
Kimball et al.

(10) Patent No.: US 8,974,447 B2
(45) Date of Patent: Mar. 10, 2015

(54) ENERGY-BASED SCISSORS DEVICE

(75) Inventors: Cory G. Kimball, Cincinnati, OH (US); Matthew C. Miller, Cincinnati, OH (US); Nicholas I. Kroscher, Mason, OH (US); Benjamin D. Dickerson, Cincinnati, OH (US); William D. Dannaher, Suzhou (CN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 428 days.

(21) Appl. No.: 13/426,084

(22) Filed: Mar. 21, 2012

(65) Prior Publication Data

US 2012/0245582 A1    Sep. 27, 2012

Related U.S. Application Data

(60) Provisional application No. 61/467,180, filed on Mar. 24, 2011.

(51) Int. Cl.
*A61B 18/04* (2006.01)
*A61B 17/28* (2006.01)
*A61B 17/29* (2006.01)
*A61B 17/32* (2006.01)

(52) U.S. Cl.
CPC ..... *A61B 17/320092* (2013.01); *A61B 17/2816* (2013.01); *A61B 2017/2929* (2013.01); *A61B 2017/320072* (2013.01)
USPC .......................................................... 606/27

(58) Field of Classification Search
CPC .... A61B 17/28; A61B 17/29; A61B 2017/29; A61B 18/1442; A61B 18/1445
USPC .......................................................... 606/27
See application file for complete search history.

(56) References Cited

U.S. PATENT DOCUMENTS

| 4,893,530 | A | | 1/1990 | Warheit |
| 5,258,006 | A | * | 11/1993 | Rydell et al. ............. 606/205 |
| 5,322,055 | A | | 6/1994 | Davison et al. |
| 5,873,873 | A | | 2/1999 | Smith et al. |
| 5,944,737 | A | | 8/1999 | Tsonton et al. |
| 5,954,736 | A | | 9/1999 | Bishop et al. |
| 5,980,510 | A | | 11/1999 | Tsonton et al. |
| 6,068,647 | A | | 5/2000 | Witt et al. |
| 6,325,811 | B1 | | 12/2001 | Messerly |
| 2004/0122433 | A1 | | 6/2004 | Loubens et al. |
| 2007/0191713 | A1 | | 8/2007 | Eichmann et al. |
| 2011/0015660 | A1 | | 1/2011 | Wiener et al. |

FOREIGN PATENT DOCUMENTS

DE   202009013504 U1   1/2010
WO   2009/046234 A2    4/2009

OTHER PUBLICATIONS

International Search Report, International Application No. PCT/US2012/029924, Dated Feb. 1, 2013.
International Preliminary Report, International Application No. PCT/US2012/029924, Dated Sep. 24, 2013.

* cited by examiner

*Primary Examiner* — Robert N Wieland
(74) *Attorney, Agent, or Firm* — Verne E. Kreger, Jr.

(57) ABSTRACT

An energy-based surgical instrument is configured to permit selective cutting, coagulation, and fine dissection required in fine and delicate surgical procedures. The scissors grip instrument provides for tube-in-tube construction so the device is useful for both open and minimally invasive procedures. The assembly includes a clamping mechanism, including a clamp arm and/or housing which are specifically configured to create a desired level of tissue clamping forces.

20 Claims, 15 Drawing Sheets

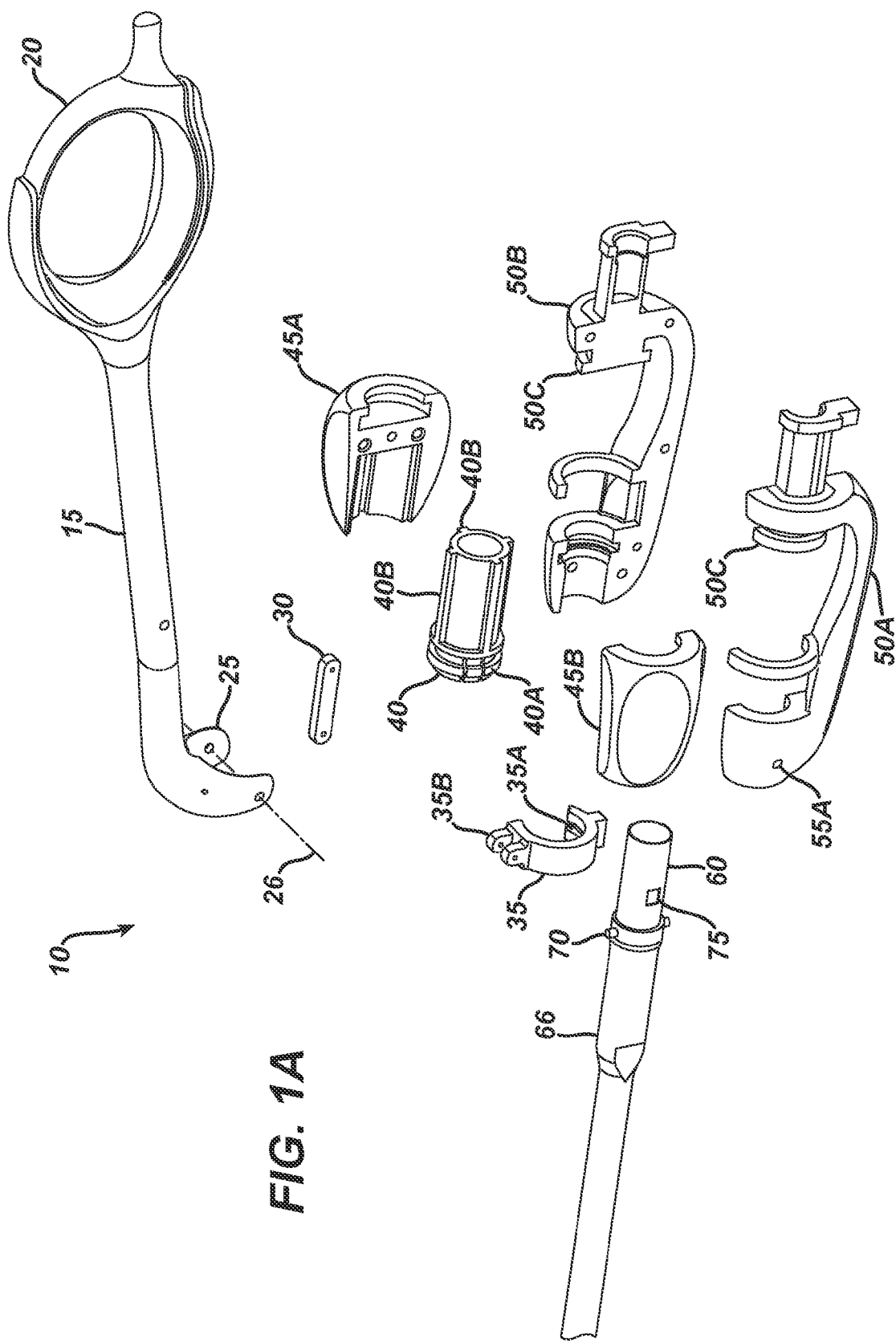

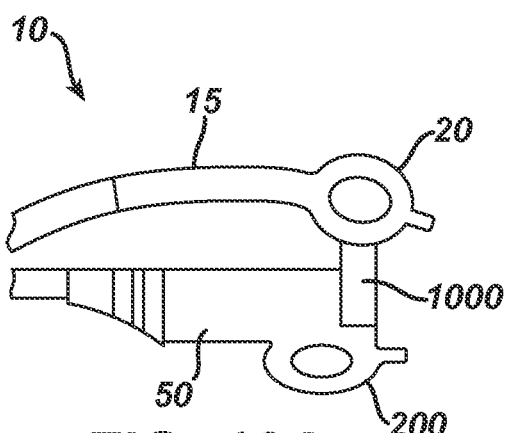 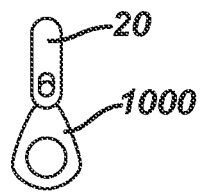
FIG. 10A    FIG. 10B
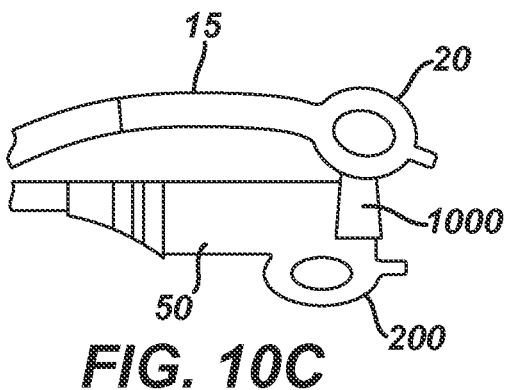 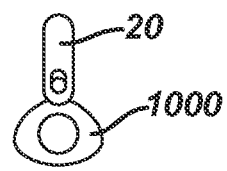
FIG. 10C    FIG. 10D

ENERGY-BASED SCISSORS DEVICE

PRIORITY

This application claims priority to U.S. Provisional Patent Application Ser. No. 61/467,180, filed Mar. 24, 2011, entitled "Ultrasonic Device for Cutting and Coagulating."

FIELD OF THE INVENTION

The present invention generally relates to surgical systems and, more particularly, to an energy-based device that is optimized to allow surgeons to perform cutting, coagulation, and fine dissection required in fine and delicate surgical procedures in both open and minimally invasive procedures.

BACKGROUND OF THE INVENTION

Energy-based surgical instruments are finding increasingly widespread applications in surgical procedures by virtue of the unique performance characteristics of such instruments. Depending upon specific instrument configurations and operational parameters, energy-based surgical instruments can provide substantially simultaneous cutting of tissue and hemostasis by coagulation, desirably minimizing patient trauma. The cutting action is typically effected by an end-effector at the distal end of the instrument, which transmits ultrasonic or RF energy to tissue brought into contact with the end-effector. Instruments of this nature can be configured for open surgical use, laparoscopic or endoscopic surgical procedures including robotic-assisted procedures.

Energy-based surgical instruments have been developed that include a clamp mechanism to hold tissue in an end-effector in order to couple ultrasonic or RF energy to the tissue of a patient. With regard to ultrasonic energy, such an arrangement (sometimes referred to as a clamp coagulator shears or an ultrasonic transector) is disclosed in U.S. Pat. Nos. 5,322,055; 5,873,873 and 6,325,811. The surgeon activates the clamp arm to press the clamp pad against an opposing jaw or blade by squeezing on the handgrip or handle.

BRIEF DESCRIPTION OF THE FIGURES

The novel features of the invention are set forth with particularity in the appended claims. The invention itself, however, both as to organization and methods of operation, may best be understood by reference to the following description, taken in conjunction with the accompanying drawings in which:

FIG. 1A is an exploded view illustrating one expression of an end-effector rotation assembly for an energy-based surgical instrument in accordance with the present invention;

FIGS. 10A-10D depict side and back views of an energy-based surgical instrument employing another expression of a force modifying member;

DETAILED DESCRIPTION OF THE INVENTION

Figure 1B:
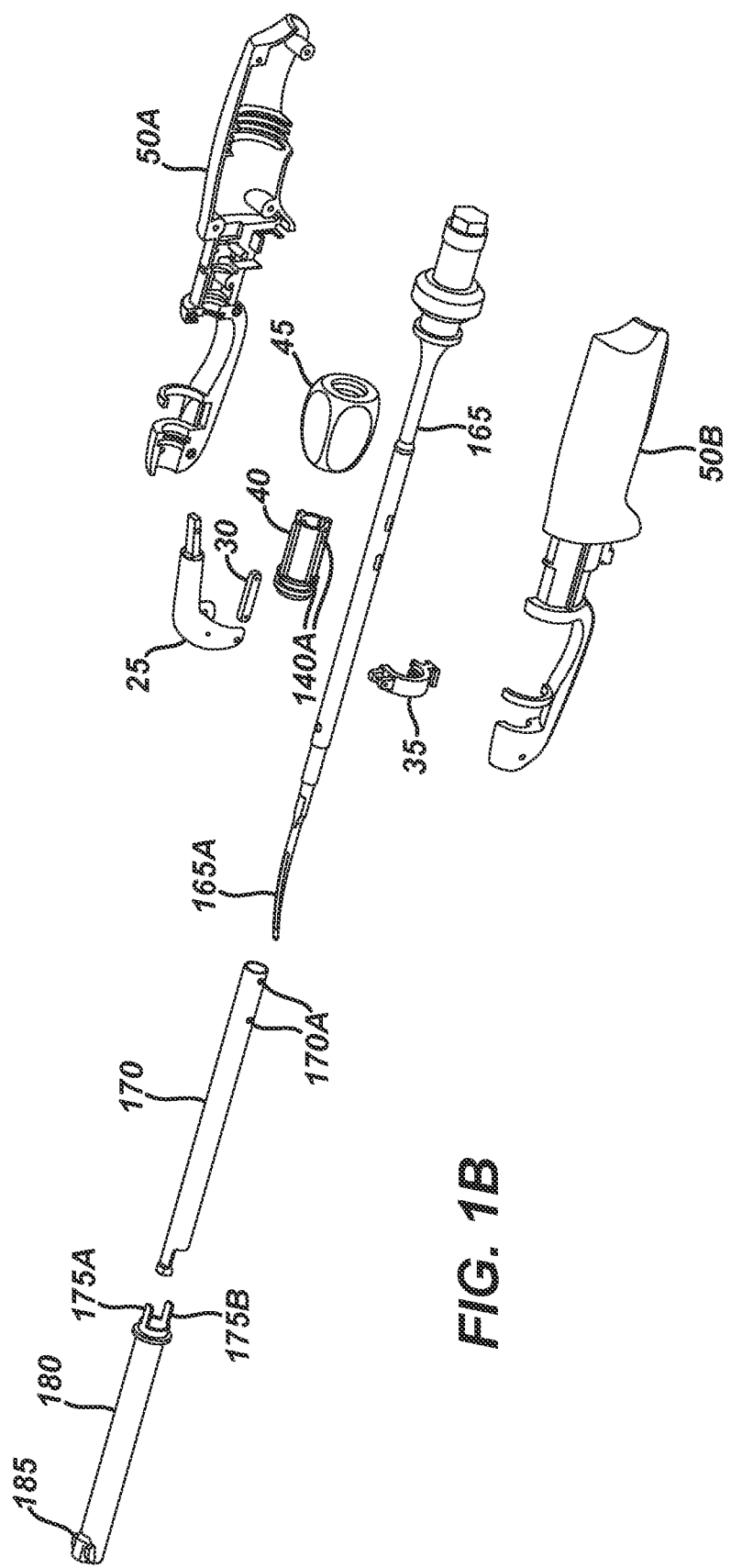
FIG. 1B is an exploded view illustrating an alternate tube-in-tube arrangement of the FIG. 1A surgical instrument in accordance with the present invention.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, etc. can be combined with any one or more of the other following-described embodiments, expressions of embodiments, examples, etc.

The present invention is particularly directed to an improved energy-based surgical clamp coagulator apparatus which is configured for effecting tissue cutting, coagulation, and/or clamping during surgical procedures, including delicate surgical procedures, both open and minimally invasive procedures. Versatile use is facilitated by selective use of dissection and application of RF or ultrasonic energy. When RF or ultrasonic components of the apparatus are inactive, tissue can be readily gripped and manipulated, as desired, without tissue cutting or damage. When the RF or ultrasonic components are activated, either separately or in unison, the apparatus permits tissue to be gripped for coupling with the energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic blade.

As will become apparent from the following description, the present clamp coagulator apparatus is particularly configured for disposable use by virtue of its straightforward construction. As such, it is contemplated that the apparatus be used in association with an ultrasonic and/or RF generator unit of a surgical system, whereby energy from the generator unit provides the desired actuation for the present clamp coagulator apparatus. It will be appreciated that a clamp coagulator apparatus embodying the principles of the present invention can be configured for non-disposable or multiple use, and non-detachably integrated with an associated generator unit. It is also appreciated that the present invention may wholly contain batteries and the energy generator in a tetherless fashion, as is known and understood in the art. See U.S. Publication 2011/0015660, the contents of which are incorporated herein by reference in its entirety.

As will become apparent from the following description, the present clamp coagulator apparatus provides an alternate embodiment for opening and closing the clamp mechanism against the blade using tube-in-tube construction. Such an embodiment may be used in place of existing scissors-type closing mechanisms in such medical devices as disclosed in U.S. Publication 2007/0191713, the contents of which are incorporated herein by reference in its entirety.

With reference to FIG. 1A, a first expression of an energy-base surgical instrument 10 is illustrated. The instrument 10 is arranged in scissor fashion and includes an actuation member 15 having a thumb ring 20 disposed at proximal end of member 15. A pivot assembly is disposed at distal end of member 15.

The energy-based surgical instrument 10 includes multi-piece handle assembly 50 comprised of handle parts or shrouds 50A, 50B which may be adapted to isolate the operator from, in the case of ultrasonic energy, vibrations of an acoustic assembly that may be located within housing 50A, 50B. Where the instrument 10 employs RF energy, housing 50 may be adapted to isolate the operator from electrical connections therein. Handle assembly 50 may be shaped to be held by a user in a conventional scissor arrangement as will be described herein. Handle 50 proximal end may be adapted to receive the distal end of an acoustic transducer (not shown). Alternatively, or in combination, handle 50 may be adapted to receive an electrical connection to an RF generator or may be adapted to hold a generator and power source for tetherless ultrasonic and/or RF operation as is know and understood in the art.

The scissor assembly set forth in FIGS. 1A and 1B (particularly handle assembly 50, actuation member 15, thumb ring 20, finger ring 200 and knob 45) may be constructed from a durable plastic, such as polycarbonate or a liquid crystal polymer. It is also contemplated that the scissor assembly may alternatively be made from a variety of materials including other plastics, ceramics or metals. Traditional unfilled thermoplastics, however, have a thermal conductivity of only about 0.20 W/m° K. (Watt/meter-° Kelvin). In order to improve heat dissipation from the instrument, the handle assembly may be constructed from heat conducting thermoplastics, such as high heat resistant resins liquid crystal polymer (LCP), Polyphenylene Sulfide (PPS), Polyetheretherketone (PEEK) and Polysulfone having thermal conductivity in the range of 20-100 W/m° K. PEEK resin is a thermoplastics filled with aluminum nitride or boron nitride, which are not electrically conductive. The thermally conductive resin helps to manage the heat within smaller instruments.

Distal end of actuation member 15 includes a pivot assembly 25 that engages annuli 55A, B on housing 50 lateral surface to permit scissor action of actuation member 15. Although shown as separate components 15, 25, it is contemplated that actuation member 15 pivot assembly 25 may be of unitary construction or may comprise sections of dissimilar material. Link 30 distal end is pivotally connected to an interior portion of pivot assembly 25 to facilitate the transfer of force from the actuation member. Proximal end of link 30 is further pivotally connected to yoke 35. Pivotal connection between pivot assembly 25 and housing 50 defines an axis 26 about which actuation member 15 rotates.

In operation, actuation member 15 is moved in a manner toward and away from handle 50 such that it pivots about axis 26 which, in turn, moves link 30 in a longitudinal distal to proximal or proximal to distal direction (dependent upon direction of actuation member 15 movement). Longitudinal movement of link 30 causes longitudinal translation of yoke 35 along a longitudinal axis 210 of handle 50 as will be more fully described herein.

Yoke 35, in one expression of the instrument 10, is annularly shaped and is further provided with a medial surface groove 35A. In one expression, yoke 35 partially encircles transfer link 40 distal end as illustrated in FIGS. 1A and 1B. Yoke 35 medial surface groove 35A is adapted to receive and engage radially projecting rail 40A of transfer link 40. Yoke 35 and rail 40A cooperate to permit rotation of transfer link 40 within yoke 35 and further permit the transfer of longitudinal force from link 30 through yoke 35 to transfer link 40.

Transfer link 40 is further provided with longitudinal rails or splines 40B that are adapted to engage medial surface longitudinal grooves 45C of rotation knob 45 (shown as rotation knob halves 45A and 45B). Rails 40B and knob grooves 45C are adapted to permit axial translation of transfer link 40 within rotation knob 45 and to permit the transfer of rotational force from rotation knob 45 to transfer link 40. To provide stability to the rotation knob 45 and transfer link 40, knob 45 is provided with a proximal annular groove 45D in knob 45 medial surface. Groove 45D is adapted to rotationally engage handle flanges 50C thereby holding rotation knob 45 in a fixed longitudinal position along longitudinal axis 210.

Still referring to FIG. 1A, instrument 10 is further provided with an end-effector shaft assembly 65. In this expression, shaft assembly 65 comprises an outer tube 66 and inner tube 60 where inner tube 60 is permitted to translate longitudinally with respect to outer tube 66.

Inner tube 60 and outer tube 66 may be pivotally connected to a clamp arm (not shown) at the distal ends of inner and outer tubes 60, 66. Inner tube 60 is sized to permit passage of an ultrasonic waveguide therethrough or an electrode conduit where instrument 10 utilizes RF energy. This clamp arm actuating tube-in-tube arrangement is disclosed in U.S. Pat. Nos. 5,944,737; 5,954,736; 5,980,510 and 6,068,647, the entire disclosures of which are incorporated herein by reference.

Inner tube 60 is provided with depression 75 that is adapted to receive a medial projection on transfer link 40 inner surface (not shown) thereby permitting the transfer of axial movement from transfer link 40 to inner tube 60. Shaft assembly 65 is provided with a pin 70 extending through apertures in outer tube 66 and inner tube 60. In this expression of instrument 10, pin 70 is substantially perpendicular to the longitudinal axis of shaft 65. To facilitate longitudinal translation of inner tube 60 relative to outer tube 66, inner tube 60 pin apertures may be longitudinally elongated. When knob 45 is rotated, transfer link 40 in turn rotates, rotating inner tube 60. Rotational force is transferred to outer tube 66 via pin 70 facilitating unitary rotation of knob 45, transfer link 40, inner tube 60 and outer tube 66.

Referring now to FIG. 1B, a second expression of an energy-based surgical instrument 10 is shown. In this expression, instrument 10 is adapted for use with an ultrasonic acoustic assembly 165. Similar to the previous expression, instrument 10 utilizes tube-in-tube construction to actuate an end-effector, which may be an ultrasonic clamp arm.

In the FIG. 1B expression, clamp force is translated from pivot assembly 25 to link 30 and to yoke 35. Yoke 35 translates longitudinally, moving transfer link 40 longitudinally in the manner described above. As depicted in FIG. 1B, transfer link 40 is provided with apertures 140A that are adapted to align with apertures 170A on inner tube 170. Pins (not shown) may be inserted into apertures 170A and 140A to join inner tube 170 to transfer link 40. Alternatively, transfer link 40 may be provided with dimples that mate with medial projections on inner tube 170. This engagement permits the transfer of longitudinal force from yoke 35 to transfer link 40 to inner tube 170, thereby actuating an end-effector.

Outer tube 180 is provided with proximal flanges 175A and 175B that engage longitudinal grooves (not shown) on the distal medial surface of transfer link 40. The distal medial grooves are sized to permit transfer link 40 to longitudinally translate along flanges 175A and 175B and to permit the transfer of rotational force from knob 45 through transfer link 40 to outer tube 180.

As illustrated in FIG. 1B, acoustic assembly 165 may be provided with an annulus and a pin passing therethrough. The pin is sized to a length greater than the diameter of acoustic assembly 165 waveguide such that end portions reside lateral to acoustic assembly 165 lateral surface. The pin is further adapted to ride in channels on the medial surface of transfer link 40 permitting the simultaneous transfer of rotational force from knob 45 to inner tube 170, outer tube 180 and acoustic assembly 165 such that a clamp arm (not shown) attached to both the inner tube 170 and outer tube 180 and ultrasonic blade 165A rotate in a fixed relative position. Such an arrangement is disclosed in U.S. Pat. No. 6,068,647 the entire disclosure of which is herein incorporated by reference.

Figure 2A:
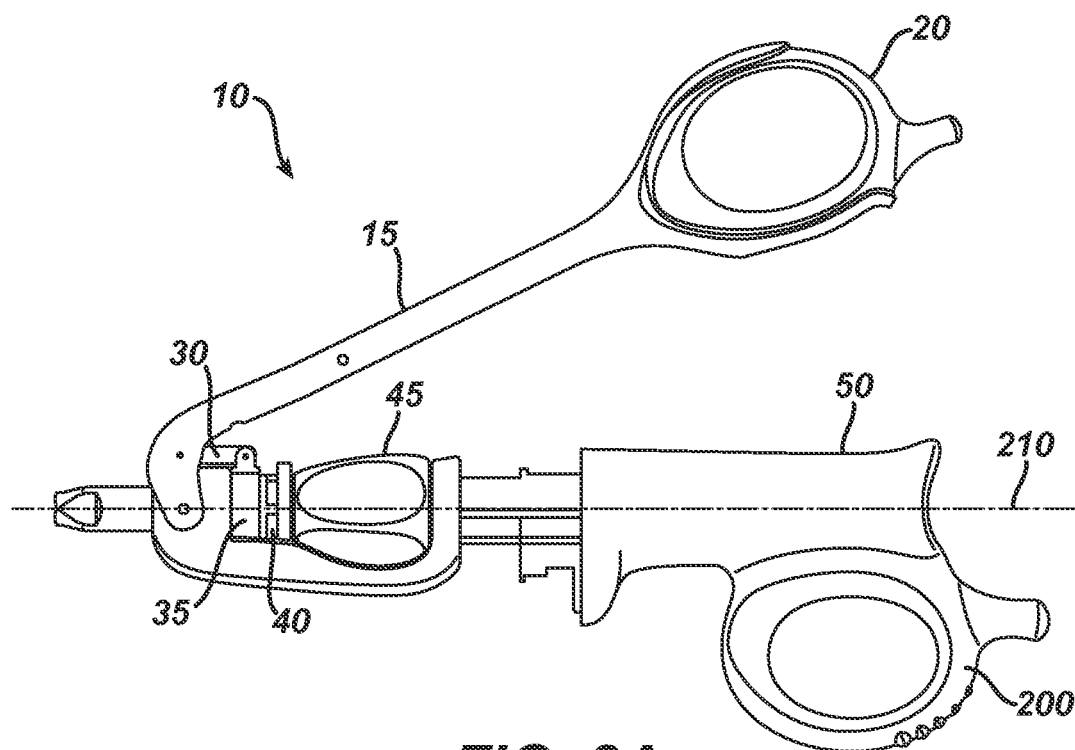
FIG. 2A is a side view of a an energy-based surgical instrument of the present invention in the open position.
Figure 2B:
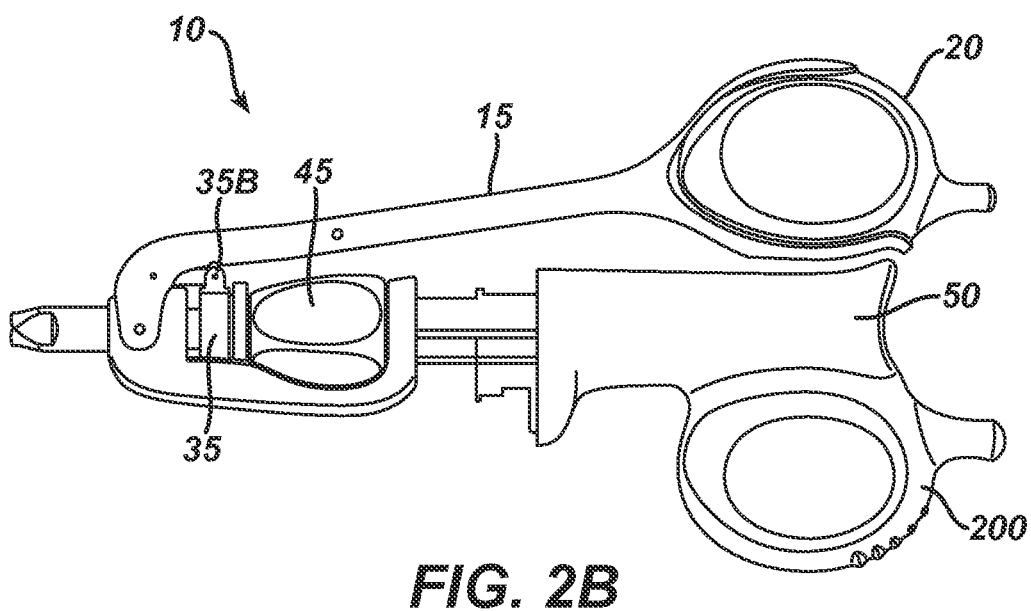
FIG. 2B depicts the FIG. 2A instrument in the closed position.
Figure 2C:
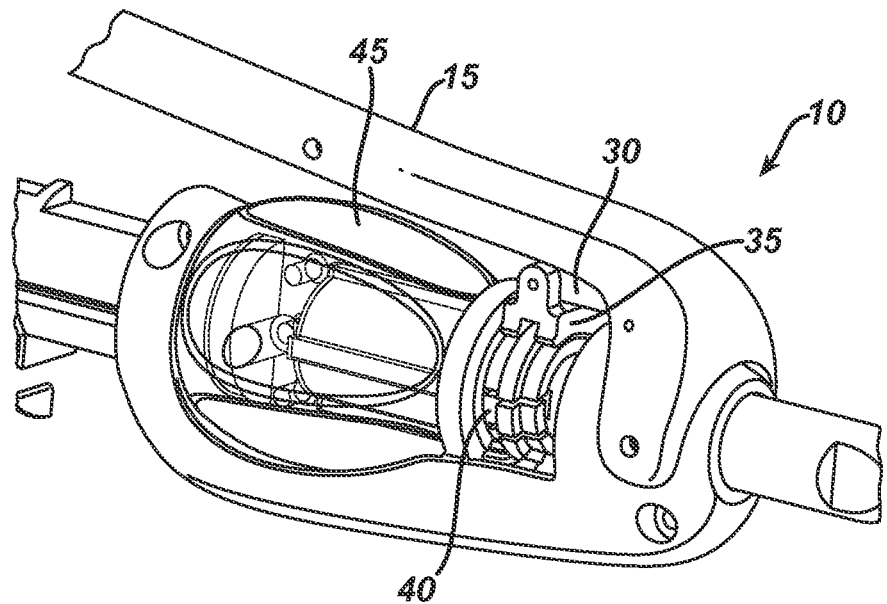
FIG. 2C is a perspective view of a rotation assembly for a scissor grip energy-based surgical instrument where the instrument is in the closed position.
Figure 2D:
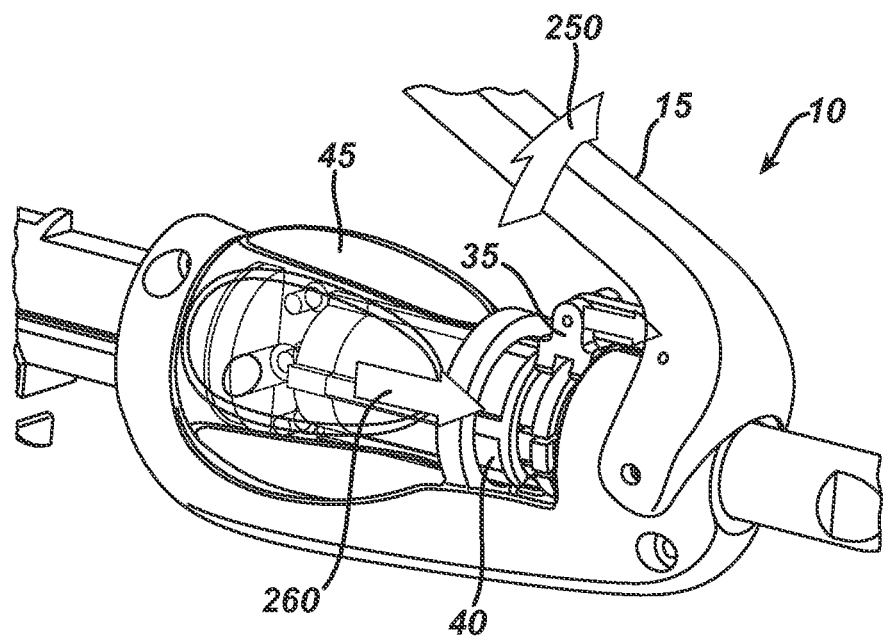
FIG. 2D is a perspective view of the FIG. 2C instrument in the open position where arrows denote the direction of movement.

FIGS. 2A and 2B depict the manner with which the drive mechanism described above converts the scissor style motion of the finger rings 20 and 200 into a lateral back and forth motion of transfer link 40 along a longitudinal axis 210 defined by outer tubes 66, 180 and housing 50. This lateral motion moves the transfer link 40 distally as shown in FIG. 2A resulting in a clamp arm opening. Similarly, closing the scissors as shown in FIG. 2B results in the transfer link translating proximally along axis 210 resulting in an end-effector clamp arm closing. FIGS. 2C and 2D show a close-up isometric cutaway view of the instrument 10 opening and closing. The direction of travel of the transfer link 40, link 30 and yoke 35 when actuation member 15 is moved away from housing 50 (denoted by arrow 250) is denoted by arrow 260 in FIG. 2D.

In use, a surgeon or operator places the instrument 10 in the palm of his or her hand. Instrument 10 may be sized to fit comfortably within a variety of adult hand sizes. The instrument 10 may be operated by placing a thumb in thumb ring 20 and opposing fingers around housing 50 and/or through finger ring 200. Opening and closing of the instrument 10 is effectuated by the surgeon moving the thumb ring away and towards the instrument, respectively. Instrument 10 is further adapted for single hand operation where the rotation knob is placed to permit the surgeon to move rotation knob 45 with the instrument 10 grasping hand index finger. When grasped by a surgeon, the actuation member 15 side of the instrument may be referred to as the top of the instrument and the handle 50, the bottom of the instrument. Handle 50 may be provided with push-buttons to permit activation of energy to an end-effector with an index or middle finger of the hand that is grasping instrument 10. Pushbuttons may be located proximal to the rotation knob 45 on the underside of handle 50 (portion of handle 50 opposite actuation member 15 denoted as reference 220) to permit the surgeon to activate the instrument with an index or middle finger. Such an embodiment permits single-handed rotation and activation of an end-effector of existing scissors-type closing mechanisms in such medical devices as disclosed in U.S. Publication 2007/0191713.

Figure 3A:
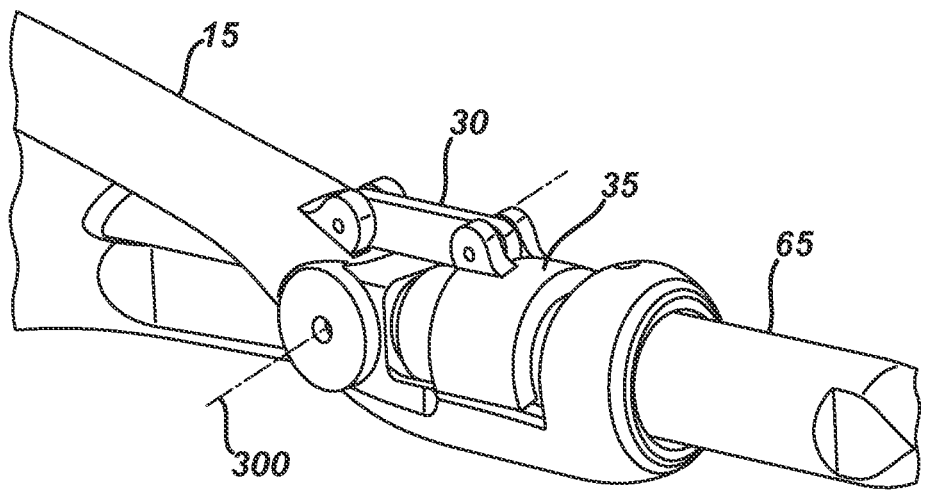
FIGS. 3A and 3B illustrate perspective views of an alternate actuation member-link arrangement in accordance with the present invention.
Figure 3B:
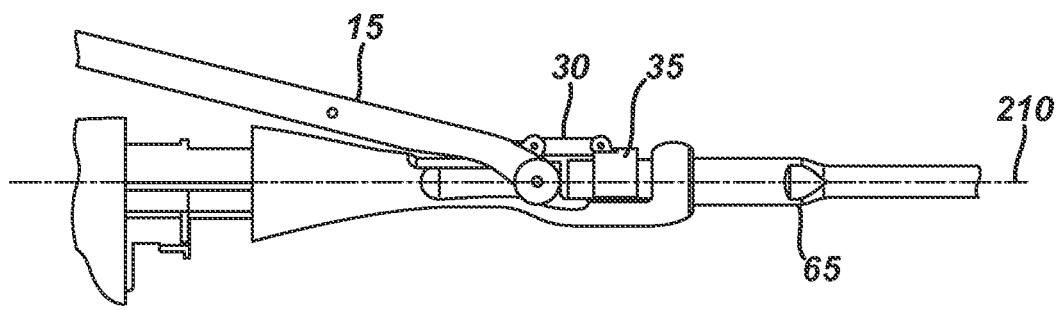

Another expression of instrument 10 is shown in FIGS. 3A and B. In this expression, the pivot axis 300 passes substantially through the longitudinal axis 210 and link 30 is attached to a top portion of actuation member 15 and distal to pivot axis 300. The FIG. 3A-B expression employs link 30 and yoke 35 to convert the opening and closing scissor motion of the device into a longitudinal back and forth motion of an inner tube.

Figure 4A:
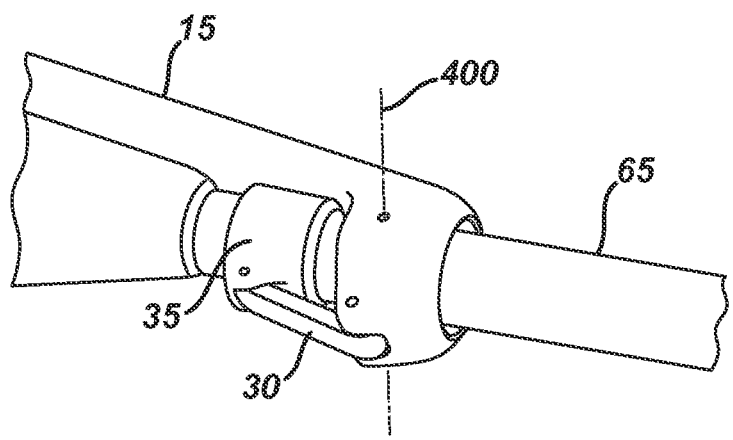
FIGS. 4A and 4B illustrate a perspective and side view of an alternate actuation member-link arrangement in accordance with the present invention.
Figure 4B:
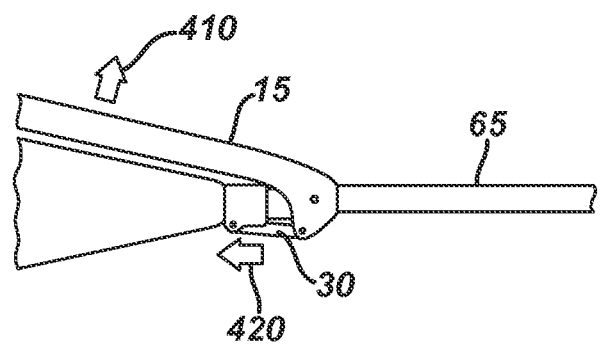

Referring now to FIGS. 4A and 4B, another expression of a force transfer assembly is depicted. In this expression, link 30 is placed on the underside of the instrument. Movement of actuation member 15 about pivot axis 400 causes link 30 to longitudinally translate yoke 35 thereby translating transfer link 40 (not shown) and inner tube 60 or 170 thereby moving a clamp disposed at the end-effector. In this arrangement, link 30 is placed on the underside of the handle 50 (towards the pinky and ring fingers of an operator) which may improve visibility for the operator.

Figure 5:
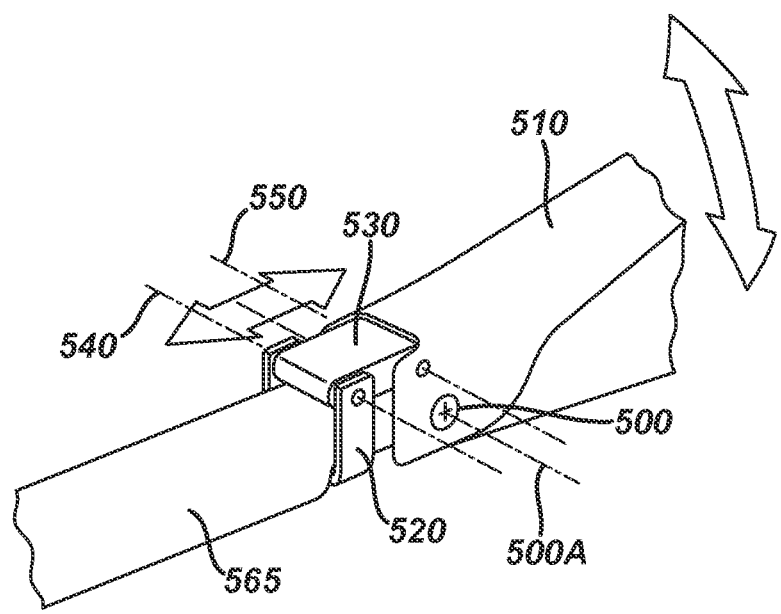
FIG. 5 is a partial perspective view of a clamp arm assembly.

The link assemblies depicted in FIGS. 3 and 4 move the link 30 and yoke 35 in longitudinal direction opposite that shown in FIGS. 1-2 due to the relative locations of the pivot axis and link 30. FIG. 5 depicts one arrangement of a tube-in-tube/clamp arm arrangement for use with the mechanisms shown in FIGS. 3-4. As shown, clamp arm 510 is pivotally attached to outer tube 565 at pivot joint 500. An inner tube, in mechanical communication with yoke 35 and transfer link 40, is provided with U-shaped bracket 520 at its distal end that is pivotally connected to clamp arm 510 via link 530. In this arrangement, longitudinal force is transferred from bracket 520 through link 530 to clamp arm 510 causing it to rotate about pivot axis 500A. The FIG. 5 clamp arm assembly may be used with the expressions of instrument 10 shown in FIGS. 1 and 2 by changing the orientation of the clamp arm 510 and bracket 520 as is known and understood in the art.

Figure 6:
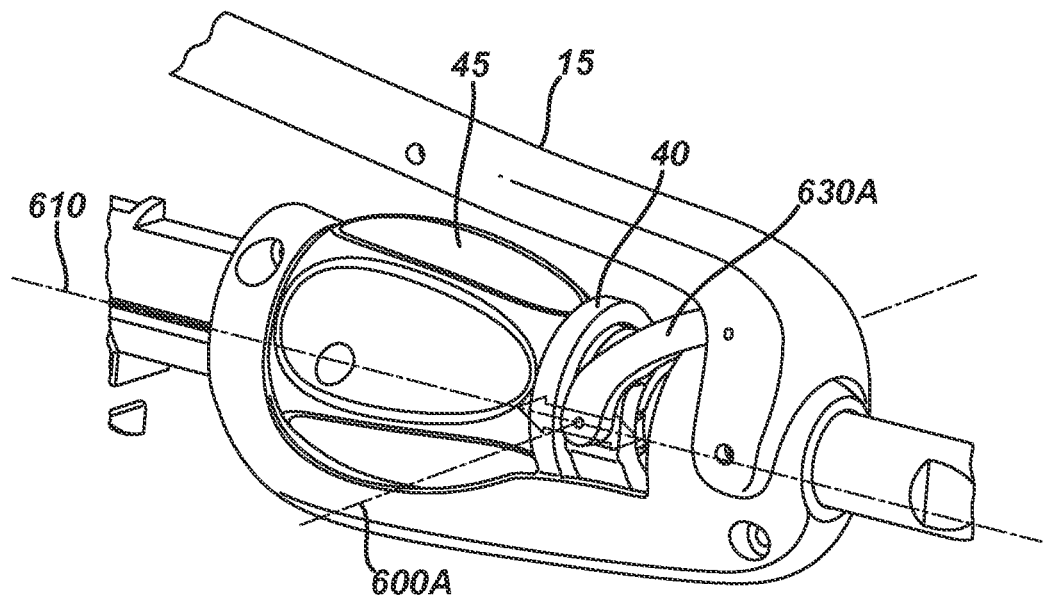
FIG. 6 is a perspective view of an alternate actuation member-link arrangement.
Figure 7:
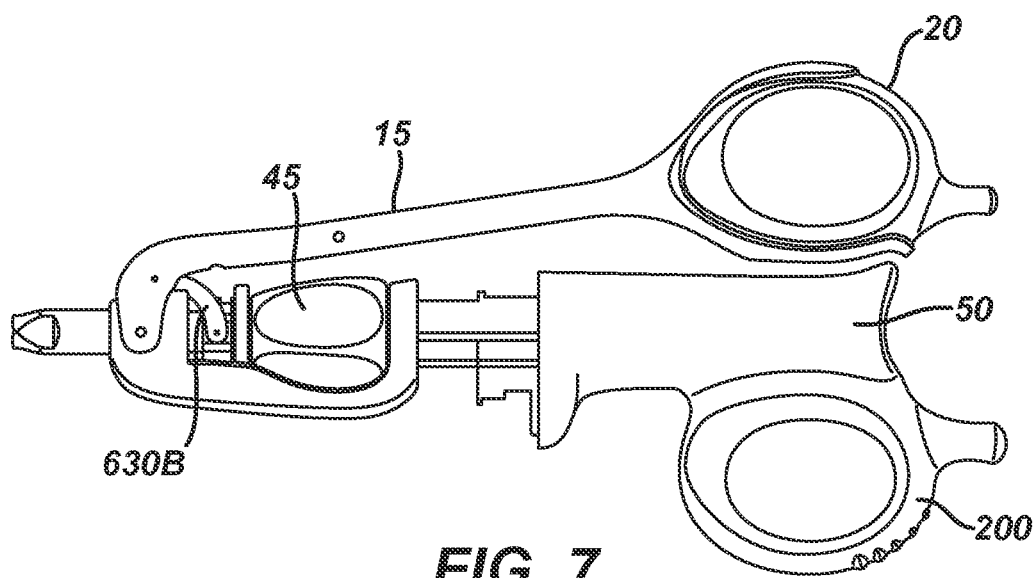
FIG. 7 is a side view of the FIG. 6 embodiment.

Referring now to FIGS. 6 and 7, another expression of a transfer link assembly is shown. In the FIG. 6 expression, instrument 10 is provided with two links 630A and 630B that attach to yoke 635 on substantially opposite lateral outer surfaces. In this arrangement, links 630A, 630B pivot about yoke 635 on an axis 600A that passes through instrument 10 longitudinal axis 610. This arrangement may have the desired effect of not imparting a rotational moment to yoke 35 which may permit a smoother transfer of forced from actuation member 15 to transfer link 40 and inner tubes 60, 170. Although the FIG. 6 expression depicts two links 630A, 630B, it is contemplated that instrument 10 may employ only one link 630A.

In the expressions discussed above, actuation member 15 pivots about a point on handle 50. It may be desirable to place a stop or fulcrum on housing 50 that actuation member 50 engages as instrument 10 is closed. In one expression, actuation member 15 contacts yoke 35 flange 35B (see FIG. 2B) which prevents thumb ring 20 from contacting or grounding to handle 50. Where actuation member 15 is comprised of rigid material, further depression of thumb ring 20 towards housing 50 will impart more force through link 30, yoke 35, transfer link 40 and eventually to a clamp arm on instrument 10 end-effector, but may not result in grounding of thumb ring 20 against handle 50. The ability to apply too much clamp pressure at the clamp arm may result in undesirable tissue effects when utilizing instrument 10 in an operative procedure. Where actuation member 15 is comprised of flexible material, thumb ring 20 may flex or bend and ground against housing 50 with the application of more force after contacting flange 35B. The amount of force applied to the clamp arm is partially determined by the location of the fulcrum with respect to the actuation member-handle pivot point as well as the composition and cross-section of the actuation member 15.

Figure 8A:
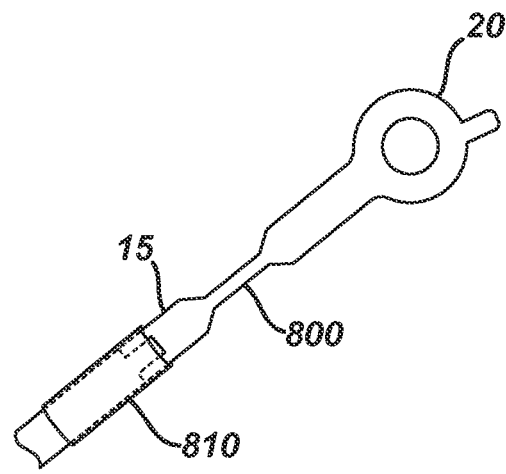
FIG. 8A is a plan view of a scissor actuation member having a force modifying sleeve in a first position.
Figure 8B:
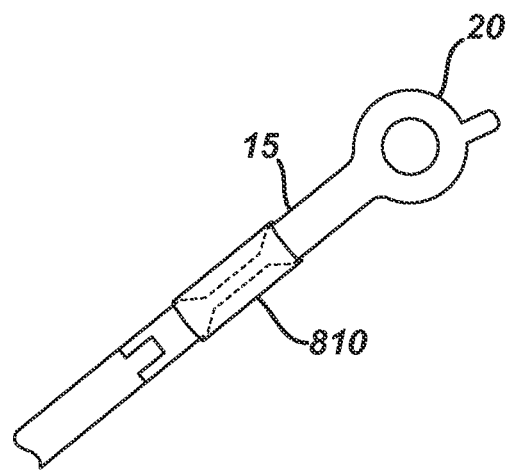
FIG. 8B depicts the FIG. 8A actuation member with the force modifying sleeve in a second position.

Referring to FIGS. 8A and 8B, an actuation member 15 is shown with narrow portion 800. In this arrangement, actuation member 15 may apply less force at the clamp arm as portion 800 may flex or bend under smaller loads due to its smaller cross section relative to the other portions of actuation member 15. When larger clamp forces are desired, a collar 810 may be moved to cover portion 800 and prevent flexing or bending, as shown in FIG. 8B. Collar 810 may be selected from a variety of materials compatible for use in a surgery and should be sized to substantially prevent bending of actuation member 15 at portion 800. It is contemplated that this actuation member may be used with any of the instrument 10 expressions shown above and may further be employed on any scissoring-type instrument. It is further contemplated that narrow portion 800 may not be the same material as actuation member 15 portions adjacent narrow portion 800.

Figure 9A:
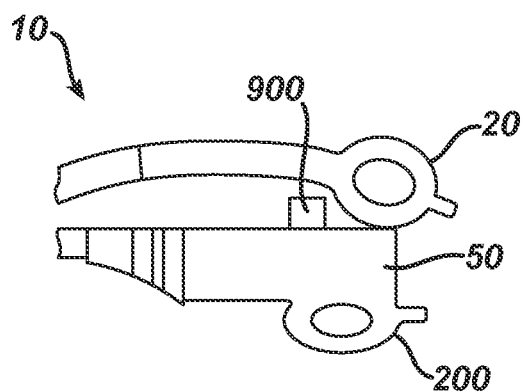
FIG. 9A is a side view of an energy-based surgical instrument depicting a force modifying actuation member stop in a first position.
Figure 9B:
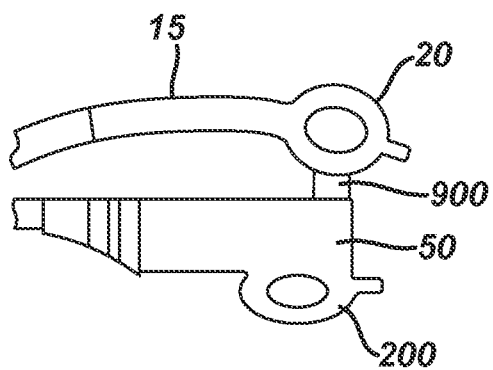
FIG. 9B depicts the FIG. 9A actuation member stop in a second position.

FIGS. 9A and 9B illustrate an alternate expression for modifying clamp force applied by actuation member 15. In this expression, instrument 10 is provided with a stop 900 that may be moved along the longitudinal axis of handle 50. Stop 900 may ride in a channel (not shown) in housing 50 that has multiple detents associated with known clamp forces at the end-effector where each detent places stop 900 at different longitudinal positions with respect to thumb ring 20. As stop 900 is moved proximal-to-distal, force imparted by actuation member 15 rises where FIG. 9B depicts minimum clamp force and FIG. 9A depicts maximum clamp force with thumb ring 20 grounded against handle 50.

FIGS. 10A-10D illustrate another expression of a clamp force modifying mechanism for use with a scissor-type instrument. Instrument 10 is provided with cam member 1000 at housing 50 proximal end. Cam member 1000 is rotationally attached to housing 50 to selectively change the grounding point of thumb ring 20 which in turn varies the amount of clamp force actuation member 15 may apply. Cam member 1000 and housing 50 may be provided with detents such that cam member 1000 annularly ratchets to fixed positions that thereby ground thumb ring at known locations associated with known clamp forces. FIG. 12B depicts a minimum clamp force arrangement while FIG. 12D depicts a maximum clamp force arrangement. It is further contemplated that cam member 1000 may be provided with steps or shelves on cam 1000 lateral surface that mate with thumb ring 20 lateral surface to permit better engagement between cam 1000 and thumb ring 20.

Figure 11A:
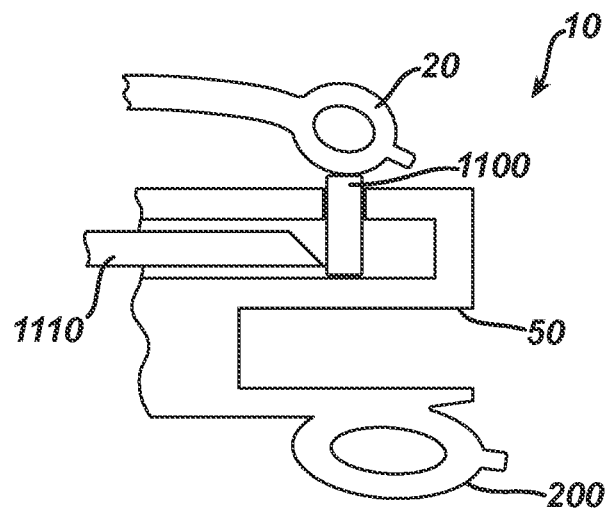
FIGS. 11A-11C depicts a plan view of another expression of a force modifying member.
Figure 11B:
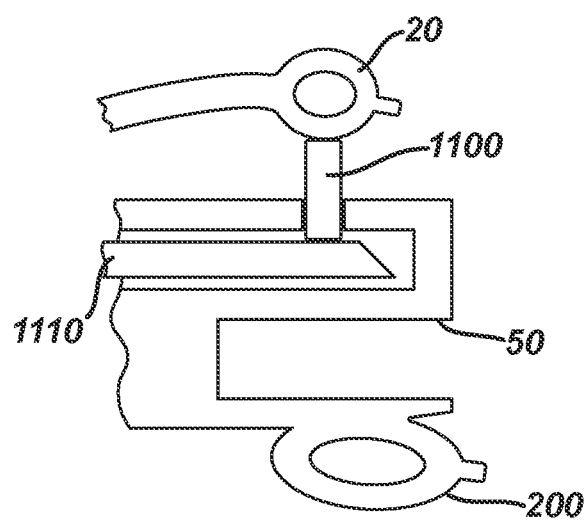
Figure 11C:
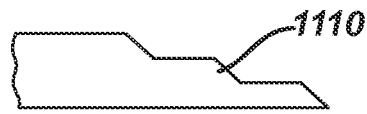

An alternate expression of the clamp force modifying mechanism is illustrated in FIGS. 11A-C. A stop pin 1100 is controlled by a slide cam 1110 to selectively engage or disengage the stop pin 1100 with the thumb ring 20 to increase or decrease the compressive forces at an end effector. The slide cam 1110 may be manually activated by placing an orthogonally projecting tab (not shown) protruding through housing 50. Tab may ride in a slot in housing 50 with detents associated with known pin 1100 heights that are further associated with known clamp forces. Alternatively, slide cam 1110 may be automated by providing a motor and gear assembly that may be controlled by a button or switch. Alternatively, the slide cam 1110 may have more than one cam ramp as shown in FIG. 11C to provide variable compressive forces at the end-effector.

Figure 12A:
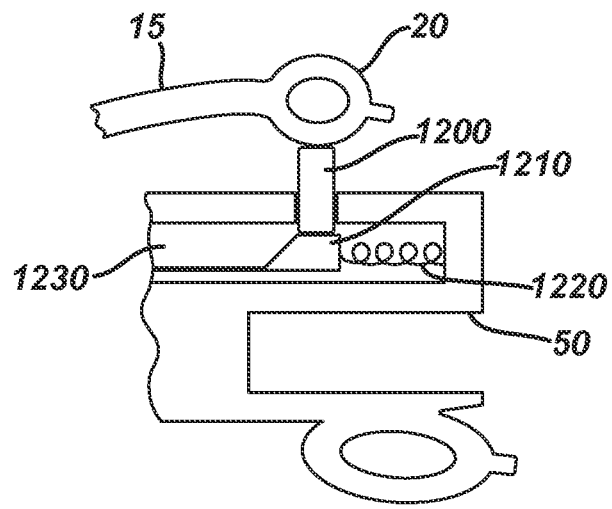
FIGS. 12A and 12B depict a side view of another expression of a force modifying member.
Figure 12B:
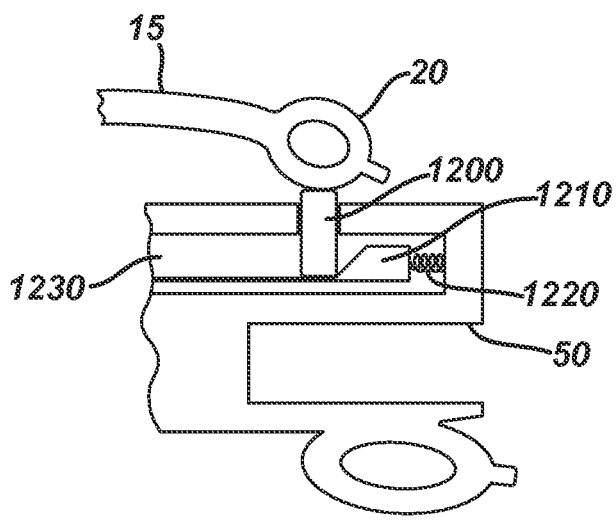

In still an alternate expression of a clamp force modifying mechanism, FIGS. 12A-B illustrate a stop pin 1200 controlled by a slide cam 1210 that is biased by a compressive spring 1220. Slide cam 1210 and spring 1220 are housed in a channel 1230 of housing 50. In a first state, the stop pin 1200 engages the thumb ring 20 to limit the compressive forces at an end effector. If the surgeon continues to press down on the stop pin 1200, the pin 1200 slides down the cam ramp and forces the slide cam 1210 to translate proximally in channel 1230 to compress the spring 1220. Pin 1230 eventually grounds against channel 1230 preventing further movement of pin 1200 as shown in FIG. 12B. Using slide cam 1210 and spring 1220, force feedback is directed to the surgeon through pin 1200 in contact with thumb ring 20. The gradual increase in force needed to compress the spring 1220 may result in variably increased compressive forces at an end-effector.

Figure 13A:
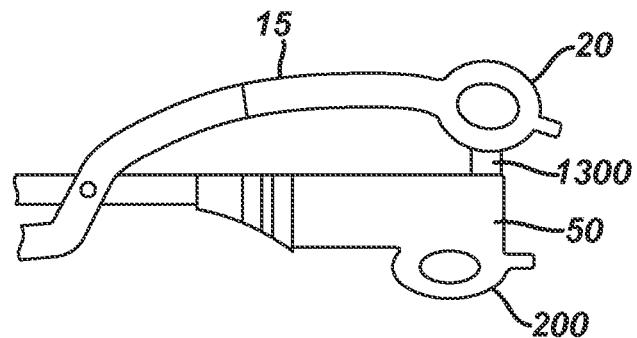
FIGS. 13A-13D depict another expression of an actuation member force modifying member.
Figure 13B:
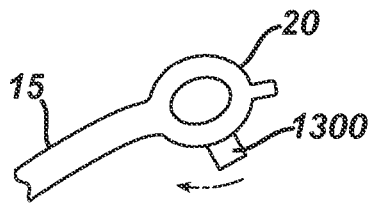
Figure 13C:
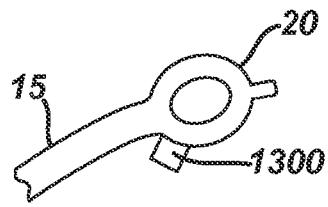
Figure 13D:
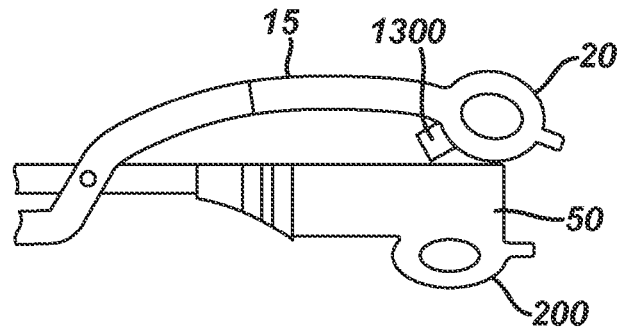

Thumb ring 20 may be provided with a movable stop pin to selectively change end-effector clamp force as illustrated in FIGS. 13A-D. Stop pin 1300 is slideably mounted to lateral lower surface of thumb ring 20. In operation, a surgeon may desire more clamp force than that available when stop pin 1300 is in a distal-most position, as depicted in FIG. 13A. By selectively rotating or moving stop pin 1300 from a distal most position, depicted in FIGS. 13B and 13C, thumb ring may be brought into contact or grounded on handle 50 as shown in FIG. 13D. Stop pin 1300, in one expression, may ride in a channel (not shown) provided in a lower portion of thumb ring 20. Although shown as a substantially rectangular, stop pin 1300 may be rounded to provided a camming surface and thumb ring 20 may be provided with detents in stop pin 1300 channel, as is known and understood in the art, to permit selective movement of stop pin 1300, further permitting selective engagement between its camming surface and handle 50, thereby incrementally changing end-effector clamp force.

Figure 14A:
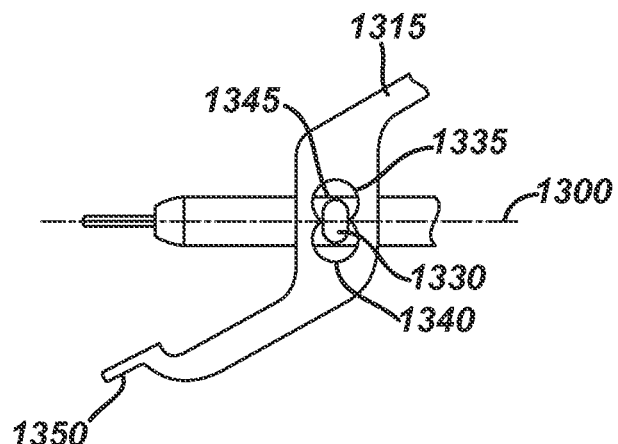
FIG. 14A is a plan view of an energy-based end-effector employing a sliding channel to modify end-effector clamp force.
Figure 14B:
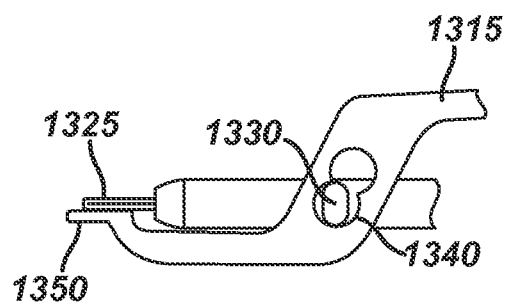
FIG. 14B depicts the FIG. 14A end-effector in a first clamping position.
Figure 14C:
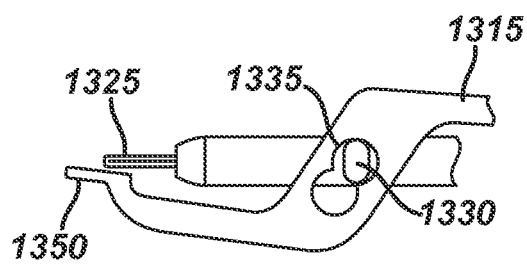
FIG. 14C depicts the FIG. 14A end-effector in a second clamping position.

In still an alternate expression of a clamp force modifying mechanism, FIGS. 14A-C illustrate an enlarged pivot slot whereby the pivot point on the actuation member maybe lengthened or shortened to change the moment arm between actuation member and handle and thus the compressive forces at the end effector.

In the FIG. 14 expression, actuation member 1315 is provided with circular apertures 1335 and 1340. As shown, apertures 1335 and 1340 radii overlap creating an enlarged pivot slot 1345 in clamp arm 1315. A stud 1330 is situated normal to end-effector shaft axis 1300. Stud 1330 is shaped to permit movement of clamp arm 1315 pivot point between aperture 1335 and 1340. As shown, stud 1330 is oval but other shapes are contemplated depending upon pivot slot 1345 configuration. In a first position, actuation member is moved to permit aperture 1340 to engage and rotate about stud 1330 as shown in FIG. 14B. This first position creates a first compressive force between end-effector 1325 and clamp 1350. In a second position, clamp arm is moved to permit pivot slot 1345 to translate relative to stud 1330 and to further permit stud 1330 to engage aperture 1335 thereby creating a second force between end-effector 1325 and clamp arm 1350 as shown in FIG. 14C. This arrangement may be employed with instrument 10 discussed previously by employing a pivot slot 1345 on both sides of pivot assembly 25 and further providing studs 1330 on lateral surfaces of housing 50 to engage pivot slots 1345.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. It is further understood that the various expressions described herein may be combined with each other, as is known and understood in the art. Accordingly, the scope of the present invention should be considered in terms of the following claims and is understood not to be limited to the details of structure, materials, or acts shown and described in the specification and drawings.

The invention claimed is:

1. A surgical instrument comprising:
a hollow outer tube defining a longitudinal axis;
a clamp arm pivotally connected to the outer tube;
an inner tube disposed substantially within the outer tube, the inner tube pivotally connected to the clamp arm and longitudinally slideable relative the outer tube;
a handle having a proximal end and a distal end disposed along the longitudinal axis;
an actuation member pivotally mounted to the handle;
a link arm pivotally attached to the actuation member;
a yoke pivotally attached to the link arm; and
a transfer link disposed about the longitudinal axis in the handle distal end, the transfer link longitudinally slideable relative to the handle and longitudinally engaging the yoke, the transfer link fixedly attached to the inner tube and rotatably engaging the outer tube.

2. The claim 1 instrument, wherein the transfer link comprises a cylinder having a medial annular surface and a lateral annular surface.

3. The claim 2 instrument, further comprising at least one rail extending longitudinally on the transfer link lateral surface.

4. The claim 3 instrument, further comprising a rotation knob disposed partially about the transfer link lateral annular surface wherein the rotation knob has at least one longitudinal medial recess that mates with the at least one transfer link rail.

5. The claim 4 instrument wherein the transfer link further comprises a raised rail disposed annularly about the transfer link distal end.

6. The claim 5 instrument wherein the yoke has an annular recess that mates with the annularly disposed transfer link raised rail.

7. The claim 6 instrument further comprising a finger ring disposed at the handle proximal end.

8. The claim 7 instrument further comprising a thumb ring disposed at the actuation member proximal end.

9. A surgical instrument comprising:
a hollow outer tube defining a longitudinal axis;
a clamp arm pivotally connected to the outer tube;
an inner tube disposed substantially within the outer tube, the inner tube pivotally connected to the clamp arm and longitudinally slideable relative the outer tube;
a handle having a proximal end and a distal end disposed along the longitudinal axis;
an actuation member pivotally mounted to the handle;
a link arm pivotally attached to the actuation member;
a yoke pivotally attached to the link arm; and
a means, fixedly attached to the inner tube and rotatingly engaging the outer tube, for transferring longitudinal force from the actuation member and a rotational force from a rotation knob.

10. The claim 9 instrument further comprising a finger ring disposed at the handle proximal end.

11. The claim 10 instrument further comprising a thumb ring disposed at the actuation member proximal end.

12. The claim 11 instrument wherein the housing proximal end is provided with a means for selectively engaging the thumb ring.

13. The claim 10 instrument further comprising a stop pin slideably attached to the thumb ring wherein the stop pin selectively engages the handle.

14. A surgical instrument comprising:
a hollow outer tube defining a longitudinal axis;
a clamp arm pivotally connected to the outer tube;
an inner tube disposed substantially within the outer tube, the inner tube pivotally connected to the clamp arm and longitudinally slideable relative the outer tube;
a handle having a lateral surface and a proximal end and a distal end, the handle disposed along the longitudinal axis, the handle having a stud disposed on the lateral surface;
an actuation member having a slot pivotally engaging the handle stud;
a link arm pivotally attached to the actuation member;
a yoke pivotally attached to the link arm; and
a transfer link disposed about the longitudinal axis in the handle distal end, the transfer link longitudinally slideable relative to the handle and longitudinally engaging the yoke, the transfer link fixedly attached to the inner tube and rotatably engaging the outer tube.

15. The claim 14 instrument wherein the slot is comprised of two circular apertures with overlapping radii.

16. The claim 15 instrument further comprising a cam rotationally attached to the handle proximal end wherein the cam selectively engages the thumb ring.

17. The claim 14 instrument further comprising a longitudinal channel in the housing, the channel having a wedge slideably mounted therein, the wedge having a camming surface engaging a stop pin, the stop pin arranged substantially normal to the channel, the channel further having a spring attached to the wedge at an end opposite the camming surface.

18. The claim 14 instrument wherein the actuation member has a first and second cross section wherein the second cross section is smaller than the first.

19. The claim 18 instrument further comprising a collar that substantially envelops the second cross section, the collar slideable relative to the actuation member.

20. The claim 19 instrument wherein the collar is slideably attached to the actuation member.

* * * * *